United States Patent [19]
Kubota et al.

[11] Patent Number: 4,867,138
[45] Date of Patent: Sep. 19, 1989

[54] RIGID ELECTRONIC ENDOSCOPE

[75] Inventors: Tetsumaru Kubota, Hachioji; Takeaki Nakamura, Hino; Minoru Okabe, Musashino; Hitoshi Karasawa, Hachioji; Hiroyuki Kusunoki, Higashimurayama; Tadao Hagino, Yokohama; Mototsugu Ogawa; Masato Toda; Teruaki Sugata, all of Hachioji; Shinichi Nishigaki, Tokyo, all of Japan

[73] Assignee: Olympus Optical Co., Ltd., Tokyo, Japan

[21] Appl. No.: 186,849

[22] Filed: Apr. 26, 1988

[30] Foreign Application Priority Data

| May 13, 1987 | [JP] | Japan | 62-116402 |
| May 18, 1987 | [JP] | Japan | 62-122292 |
| May 19, 1987 | [JP] | Japan | 62-121755 |
| Feb. 10, 1988 | [JP] | Japan | 63/030585 |

[51] Int. Cl.[4] .............................................. A61B 1/06
[52] U.S. Cl. ........................................... 128/6; 358/98
[58] Field of Search ..................... 128/4, 6, 7; 358/98

[56] References Cited

U.S. PATENT DOCUMENTS

| 1,747,407 | 2/1930 | Wappler | 128/6 |
| 3,835,842 | 9/1974 | Iglesias | 128/7 |
| 3,886,933 | 6/1975 | Mori et al. | 128/7 |
| 4,491,865 | 1/1985 | Dominick Danna et al. | 128/4 X |
| 4,604,992 | 8/1986 | Sato | 128/6 |

Primary Examiner—William H. Grieb
Attorney, Agent, or Firm—Armstrong, Nikaido, Marmelstein, Kobovcik & Murray

[57] ABSTRACT

This rigid electronic endoscope is formed of an endoscope body and an elongate tubular guide tube. An insertable part to be inserted through the guide tube is provided in front of this endoscope body. A solid state imaging device as an imaging means is provided in the tip part of this insertable part and a supporting part of a cross-sectional area smaller than of this tip part is provided in the rear of this tip part. A space as a treating tool inserting path or as a liquid feeding and sucking tube path which can feed and drain an irrigating liquid is formed between this supporting part and the inner surface of the guide tube.

28 Claims, 10 Drawing Sheets

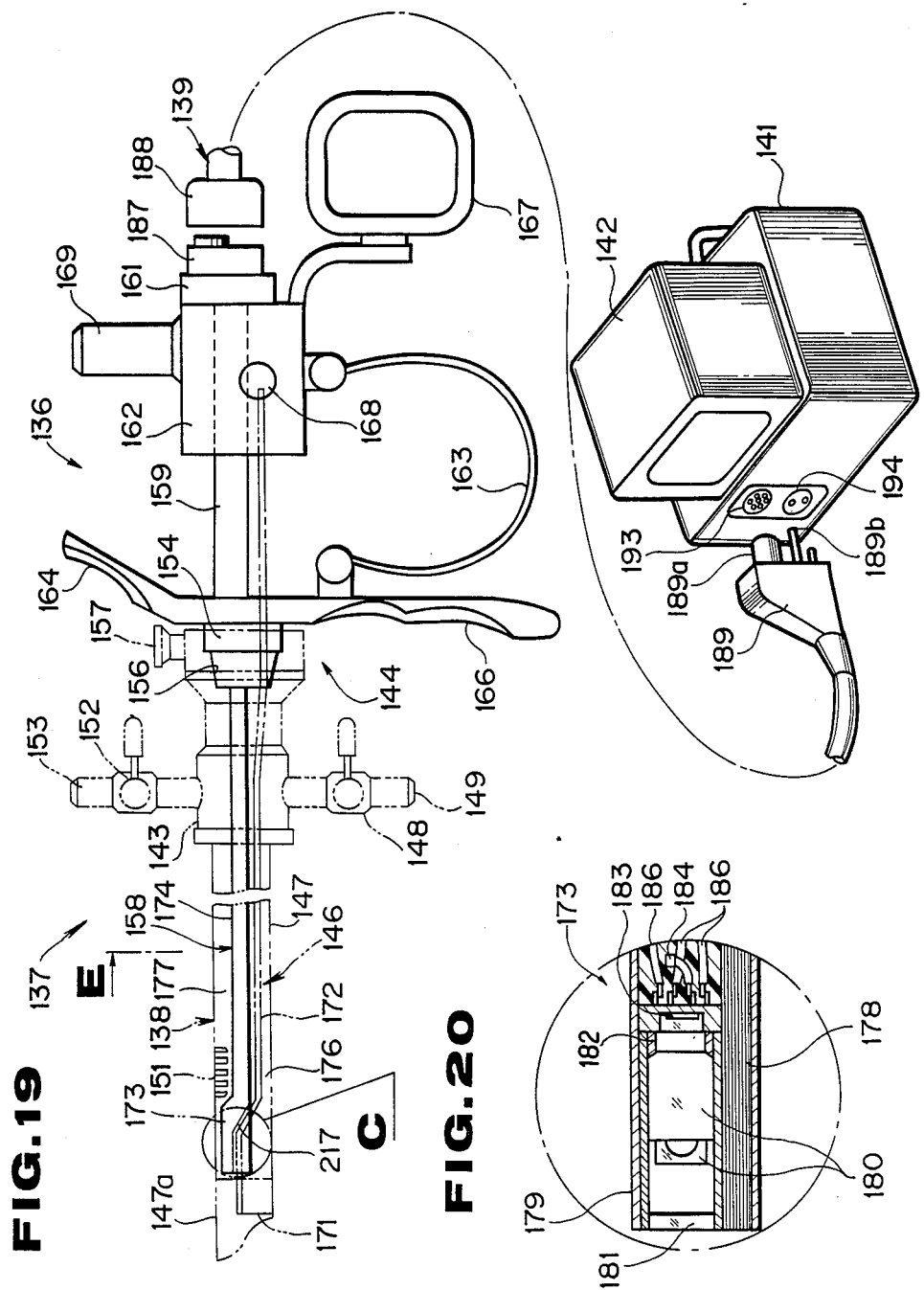

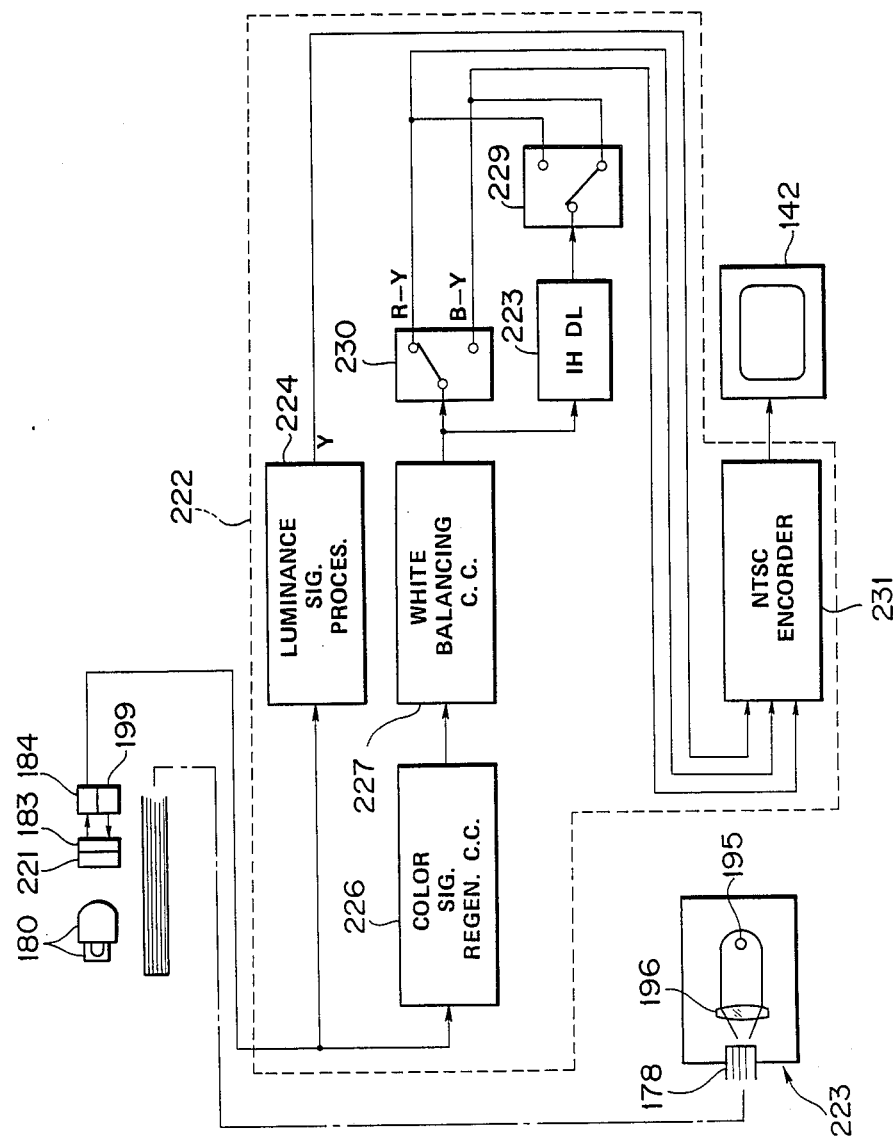

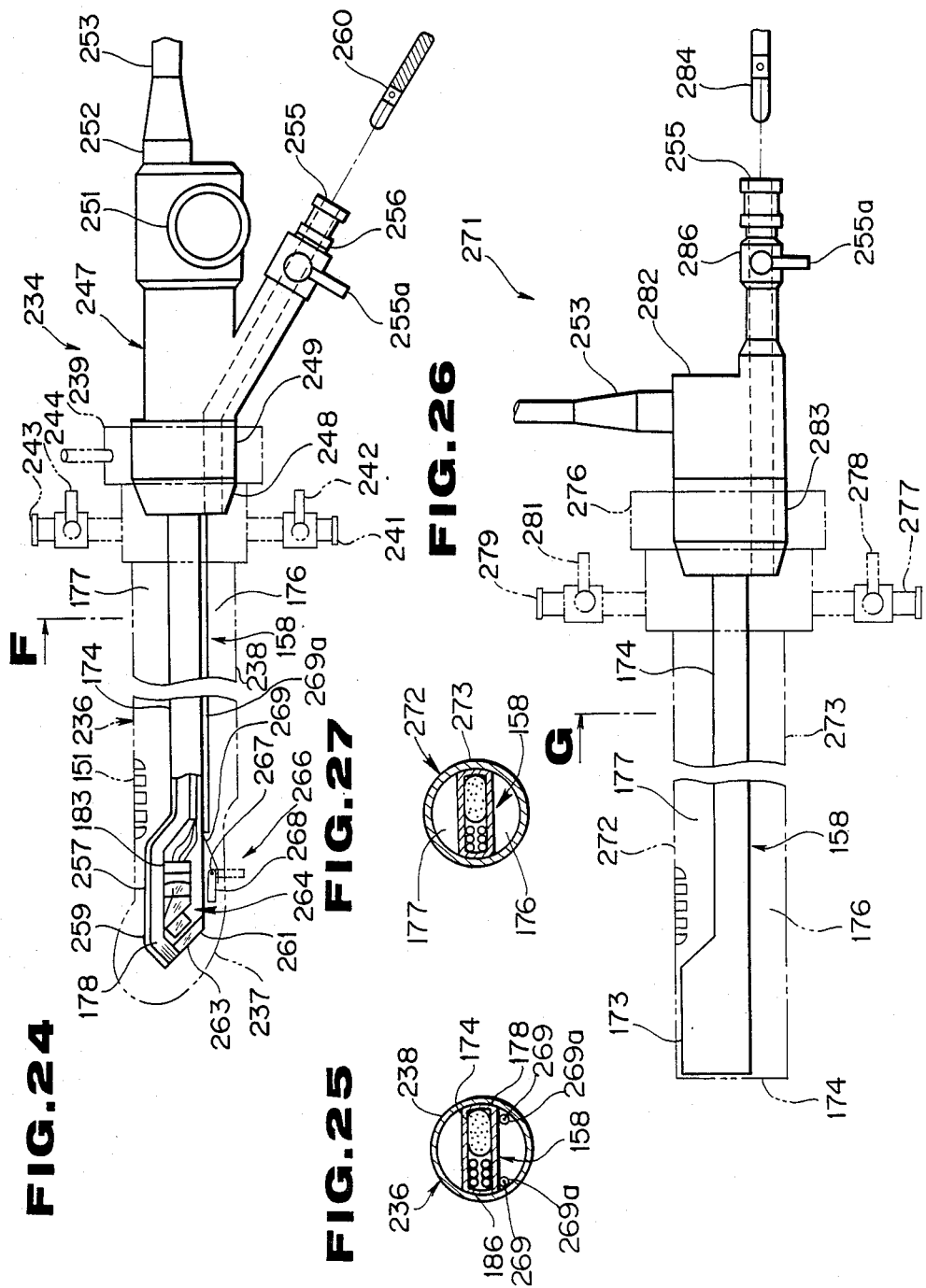

RIGID ELECTRONIC ENDOSCOPE

FIELD OF THE INVENTION

This invention relates to a rigid electronic endoscope wherein the outside diameter of the base side is made smaller than of the tip part and a treating tool and irrigating liquid can be fed and drained.

BACKGROUND OF THE INVENTION

Recently, there is extensively used an endoscope whereby organs within a body cavity can be observed by inserting an insertable part of a small diameter into the body cavity and various cures can be made by using a treating tool inserted through a treating tool channel as required.

Among the above mentioned endoscopes, there are a flexible endoscope wherein the insertable part is flexible and can be passed through a bent course from a mouth cavity or the like to observe an object position within a body cavity and a rigid endoscope wherein the insertable part is rigid and is inserted substantially straight.

Further, there are recently suggested various electronic endoscopes wherein each solid state imaging device as a charge coupled device (CCD) is used as an imaging means. Such electronic endoscope has advantages that the resolution is higher than in a fiber scope, it is easy to record and reproduce picture images and such treatments of picture images as the magnification of picture images and the comparison of two pictures are easy.

Now, in the above mentioned rigid endoscope or, for example, a bladder-urethra scope for diagnosing and curing the bladder or urethra, an optical viewing tube (telescope) or, as required, such treating tool as a catheter or forceps is inserted through a sheath as a hollow guide tube inserted into the urethra to make a treatment.

Further, in case the above mentioned rigid endoscope is to be inserted, a hollow sheath is inserted into the urethra and the rigid endoscope is inserted with this sheath as a guide. At this time, an irrigating liquid is required to be fed to the periphery of the affected part through a hollow path between the sheath and endoscope and to be sucked and drained to discharge a body liquid or the like obstructing the observation or diagnosis of the affected part. In the case of incising the swollen prostate with a resectoscope having a handle and optical viewing tube inserted through the sheath, it may be necessary to drain out of the body the incised tissue pieces and blood together with the irrigating liquid. In such case, the irrigating liquid has been fed through an irrigating liquid path formed in the hollow clearance between the inner peripheral surface of an inner sheath having a cylindrical or elliptical cross-section and the outer peripheral surface of the scope having an elliptical outside diameter and inserted through the sheath. This is accomplished by making the sheath in a double structure and has been drained through an irrigating liquid path formed in the hollow clearance between the outer peripheral surface of the sheath and the inner peripheral surface of an outer sheath having a cylindrical cross-sectional shape and having the inner sheath inserted through it.

However, when, as mentioned above, the optical viewing tube and treating tool or the like are inserted through the inner sheath, further the outer sheath is made to cover the inner sheath and the irrigating liquid is fed and drained through such hollow clearance, in case a treating tool of a large diameter is to be inserted, the hollow clearance will become smaller and the amount of the irrigating liquid will also become smaller. Therefore, there have been problems that, in case a treating tool of a large diameter and a large amount of an irrigating liquid are required, the inner and outer sheath diameters must be made large and the pain given to the patient will increase.

OBJECT AND SUMMARY OF THE INVENTION

An object of the present invention is to provide a rigid electronic endoscope wherein, even in case a treating tool of a large diameter and a large amount of an irrigating liquid are required, without making the diameter of the sheath large, the irrigating liquid can be continuously fed and drained and the affected part can be treated with little pain given to the patient.

The rigid electronic endoscope of the present invention comprises a rigid insertable part and a holding part connected to the base side of this insertable part. This insertable part has a tip part provided with a solid state imaging device and a supporting part connected to the base side of this tip part and having a cross-section smaller than of the above mentioned tip part. This insertable part is inserted through a guide tube to form a treating tool inserting path or an irrigating liquid feeding and sucking tube path between the inner surface of the guide tube and the supporting part.

BRIEF DESCRIPTION OF THE DRAWINGS

FIG. 1 is a side view showing an entire rigid electronic endoscope apparatus.

FIG. 2 is a sectioned view showing a tip part of the rigid electronic endoscope.

FIG. 3 is a sectioned view on line A—A' in FIG. 2.

FIG. 9 is an explanatory view showing the formation of a rigid electronic endoscope.

FIG. 10 is an elevation of a tip part of the rigid electronic endoscope.

FIG. 12 is an explanatory view showing the formation of a rigid electronic endoscope.

FIG. 13 is a magnified elevation of a tip surface of the rigid electronic endoscope.

FIG. 14 is a magnified sectioned view on line B—B' in FIG. 12.

FIG. 15 is a sectioned view showing the formation of the tip of a rigid electronic endoscope.

FIG. 16 is a magnified elevation of a tip part of the rigid electronic endoscope.

FIG. 17 is a sectioned view showing the formation of the tip side of a rigid electronic endoscope.

FIG. 18 is a magnified elevation of a tip part of the rigid electronic endoscope.

FIGS. 19 to 22 relate to the twelfth embodiment of the present invention.

FIG. 19 is a formation view of an entire electronic resectoscope.

FIG. 20 is a detailed view of the part C in FIG. 19.

FIG. 21(a) is a sectioned view in the direction D in FIG. 19.

FIG. 21(b) is a magnified elevation of a tip part.

FIG. 22 is a block diagram of a video signal processing circuit of a field sequential system.

FIG. 23 relates to a modification of the twelfth embodiment and is a block diagram of a video signal processing circuit of a synchronous system.

FIGS. 24 and 25 relate to the thirteenth embodiment of the present invention.

FIG. 24 is a formation view of a rigid electronic endoscope.

FIG. 25 is a sectioned view in the direction F in FIG. 24.

FIG. 26 relates to the fourteenth embodiment of the present invention and is a formation view of a rigid electronic endoscope.

FIG. 27 is a selected view in the direction G in FIG. 26.

DETAILED DESCRIPTION OF PREFERRED EMBODIMENTS

Embodiments of the present invention shall be explained in the following with reference to the drawings.

Figure 1:
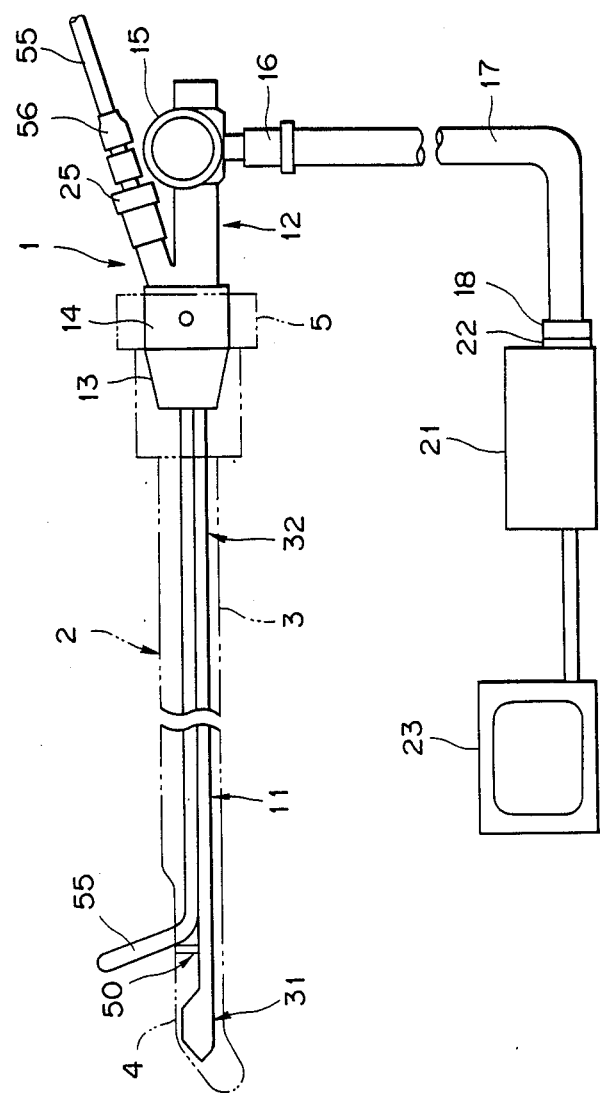
FIGS. 1 to 3 relate to the first embodiment of the present invention.
Figure 2:
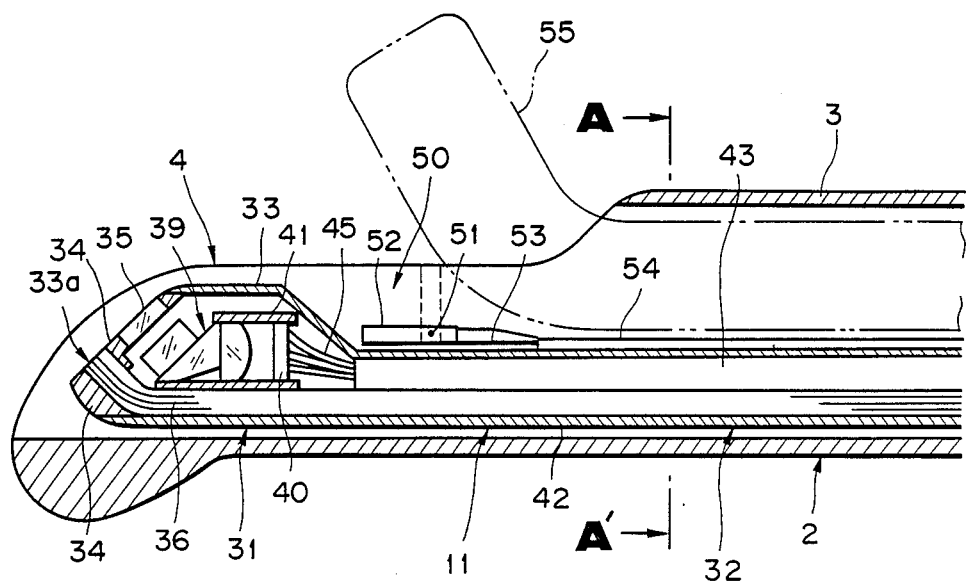
Figure 3:
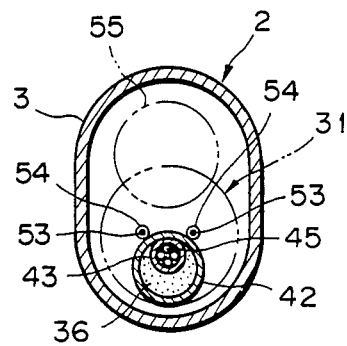

FIGS. 1 to 3 show the first embodiment of the present invention.

As shown in FIG. 1, a rigid electronic endoscope 1 of this embodiment is to be used as combined with a sheath 2. The above mentioned sheath 2 has an elongate hollow tube part 3, for example, substantially elliptic in the cross-section as shown in FIG. 3. In the tip part of this hollow tube part 3, as shown in FIG. 2, an opening 4 for observation and treating tools is formed from the tip to the upper side. The above mentioned sheath 2 is provided at the rear end with a connecting part 5 to which the above mentioned rigid electronic endoscope 1 can be removably connected. By the way, the above mentioned sheath 2 is provided in the rear part with an irrigating part not (illustrated) through which an irrigating liquid can be introduced into the sheath 2.

On the other hand, the above mentioned rigid electronic endoscope 1 is provided with a rigid elongate insertable part 11 to be inserted through the hollow tube part 3 of the above mentioned sheath 2 and an operating part 12 connected to the rear end of this insertable part. The above mentioned operating part 12 is provided at the front end with a tapered part 13 small in the diameter on the tip side to be fitted into the connecting part 5 of the above mentioned sheath 2 and a connecting part 14 to be connected to the above mentioned connecting part 5 adjacently to the rear of the tapered part 13. Also, the above mentioned operating part 12 is provided on the rear end side with a wire operating knob 15 and a light guide mouthpiece 16 which is also a signal connector. A light guide cable 17 internally fitted with a signal cable is to be connected to the above mentioned light guide mouthpiece 16. The above mentioned light guide cable 17 is provided at the tip with a connector 18 to be connected to a connector receptacle 22 of a control apparatus 21 containing a light source apparatus and signal processing circuit. A color monitor 23 as a displaying means is to be connected to the above mentioned control apparatus 21.

The above mentioned operating part 12 is provided with a treating tool inserting part body 25 as branched obliquely rearward with respect to the axial direction of the insertable part 11.

Now, in this embodiment, as shown in FIG. 1, the above mentioned insertable part 11 is formed of a tip part 31 of a large diameter and a small diameter part 32 smaller in the outside diameter than the above mentioned tip part. By the way, the above mentioned small diameter part 32 is to be inserted eccentrically on the lower side within the hollow tube part 3 of the sheath 2.

As shown in FIG. 2, the above mentioned tip part 31 is provided with a rigid tip part body 33. A sloped opening 33a opening on the opening 4 side of the above mentioned sheath 2 is formed at the tip of this tip part body 33 and is fitted with a cover glass 35 and a light guide (of fibers) 36 at the tip through a cover member 34. An objective lens system 39 which is opposed to the above mentioned cover glass 35, in which the observing visual field direction has a predetermined angle with the axial direction of the insertable part 11 directed through the opening 4 of the above mentioned sheath 2 and which is set in an obliquely forward direction is contained within the above mentioned tip part body 33. A solid state imaging device 40 as an imaging means is arranged in the range forming position of this objective lens system 39. By the way, the above mentioned objective lens system 39 and solid state imaging device 40 are supported and fixed by a supporting frame 41.

On the other hand, as shown in FIG. 3, the above mentioned small diameter part 32 is connected to the rear end of the above mentioned tip part body 33 and has an outer pipe 42 smaller in the outside diameter than the above mentioned tip part body 33 and an inner pipe 43 inserted upward eccentrically within this outer piper 42. As shown in FIG. 3, signal lines 45 connected to the above mentioned solid state imaging device 40 are inserted through the above mentioned inner pipe 43. The above mentioned light guide 36 is inserted between the above mentioned outer pipe 42 and inner pipe 43. The above mentioned signal lines 45 and light guide 36 are connected to the above mentioned light guide mouthpiece 16 provided on the operating part 12 through the above mentioned small diameter part 32.

In this embodiment, a treating tool raising device (called also a heaver) 50 is provided on the side corresponding to the opening 4 of the above mentioned sheath 2 on the tip side of the above mentioned small diameter part 32 and is provided with a raising stand 52 rotatable on the tip side with a rotary shaft 51 as a center and, for example, two operating wire 53 operating to rotate this raising stand 52. As shown in FIG. 3, the above mentioned operating wires 53 are inserted through respective wire tubes 54 arranged in the axial direction above the above mentioned outer tube 42 and are connected to the wire operating knob 15 provided on the above mentioned operating part 12. By rotating this wire operating knob 15, the above mentioned raising stand 52 is rotated, as shown in FIG. 2, such treating tool 55 as a catheter or forceps is raised on the tip side and, in the rear position of the tip part 31, the above mentioned treating tool 55 can be projected in the tip part sidewise from the opening 4 of the above mentioned sheath 2. By the way, the above mentioned treating tool 55 is inserted for example, through a catheter mouthpiece 56 from the treating tool inserting part 25.

Now, in case a field sequential system is used as a color imaging system, the light source apparatus provided within the above mentioned control apparatus 21 will be provided, for example, with a light source lamp and a rotary color filter arranged on the front surface side of this light source lamp and having filters transmitting such respective colors as red (R), green (G) and blue (B). The illuminating light emitted from the above mentioned light source lamp will be made lights of respective wavelengths, of R, G and B in turn through the above mentioned rotary color filter, will be condensed by a condenser lens and will enter the entrance end of the light guide 36 of the rigid endoscope 1 through the light guide cable 17 connected to the above mentioned control apparatus 21. On the other hand, in case a synchronous system is used as a color imaging system, the white light emitted from the white light source will enter the entrance end of the above mentioned light guide 36. The illuminating light will be led to the tip part 31 by the above mentioned light guide 36, will be emitted from the exit end and will be radiated onto an object to be imaged.

The object image by the above mentioned illuminating light will be formed on the solid state imaging device 40 by the objective lens system 39 and will be photoelectrically converted by this solid state imaging device 40. This solid state imaging device 40 is driven by the driving circuit provided within the above mentioned control apparatus 21. The read out signal will be input into the signal processing circuit provided within the above mentioned control apparatus 21. A video signal will be produced by this signal processing circuit and will be input into the color monitor 23 and the object image will be displayed in this color monitor 23.

By this way, in case a synchronous system is used as a color imaging system, a color filter array in which color filters respectively transmitting such respective colors as R, G and B are arranged in the form of a mosaic will be provided on the front surface of the imaging surface of the above mentioned solid state imaging device 40.

Thus, in the rigid electronic endoscope 1 of this embodiment, the solid state imaging device 40 as an imaging means is provided in the tip part 31 of the insertable part 11 and the outside diameter of the small diameter part 32 on the base side is made smaller than the outside diameter of the above mentioned tip part 31. The above mentioned small diameter part 32 through which the signal lines 45 and light guide 36 are inserted but such optical image transmitting means as the relay lens system and image guide fibers are not inserted can be made thinner than in the conventional rigid optical endoscope.

Therefore, the path of the treating tool 55 formed in the clearance between the above mentioned small diameter part 32 and the inner peripheral surface of the sheath 2 can be made larger than in the past and the treating tool 55 of a large diameter can be used without using the sheath 2 of a large diameter.

Figure 4:
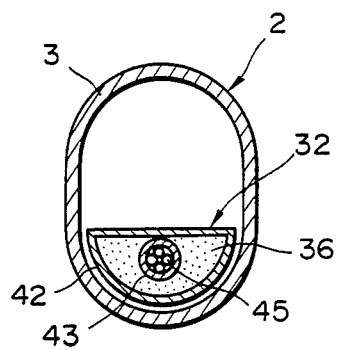
FIG. 4 is a sectioned view showing a small diameter part of an insertable part of a rigid electronic endoscope relating to the second embodiment of the present invention.

FIG. 4 is a sectioned view showing a small diameter part of an insertable part of a rigid electronic endoscope relating to the second embodiment of the present invention.

In this embodiment, the cross-sectioned shape of the outer pipe 42 forming the small diameter part 32 of the insertable part 11 is formed to be substantially of a semi-circle flat on the upper side and this small diameter part 32 is eccentrically inserted on the lower side within the hollow tube part 3 of the sheath 2.

According to this embodiment, a thicker treating tool 55 can be inserted at a high space efficiency between the small diameter part 32 and the inner peripheral surface of the sheath 2 without making the cross-sectional area of the light guide 36 smaller than in the case of making the cross-section of the outer pipe 42 circular.

Figure 5:
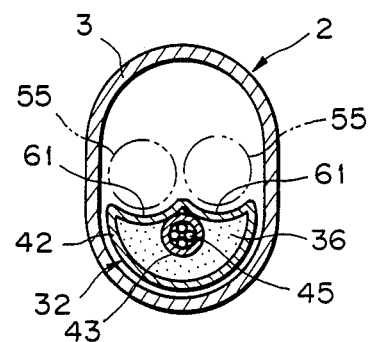
FIG. 5 is a sectioned view showing a small diameter part of an insertable part of a rigid electronic endoscope relating to the third embodiment of the present invention.

FIG. 5 is a sectioned view showing a small diameter part of an insertable part of a rigid electronic endoscope relating to the third embodiment of the present invention. In this embodiment, for inserting two treating tools 55 through a sheath 2, two recesses 61 are formed in the outer pipe 42 of the small diameter part 32 at its upper portion forming guides for the two treating tools 55.

Figure 6:
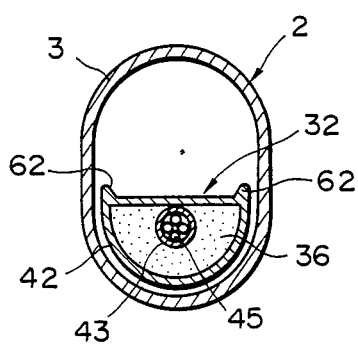
FIG. 6 is a sectioned view showing a small diameter part of an insertable part of a rigid electronic endoscope relating to the fourth embodiment of the present invention.

FIG. 6 is a sectioned view showing a small diameter part of an insertable part of a rigid electronic endoscope relating to the fourth embodiment of the present invention.

In this embodiment, the same as in the second embodiment, the cross-sectioned shape of the outer pipe 42 is made substantially semicircular and convexes 62 are provided in the axial direction on both end edges of the flat surface on the upper side and are made guides for the treating tools 55.

Figure 7:
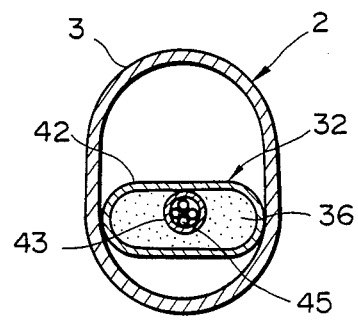
FIG. 7 is a sectioned view showing a small diameter part of an insertable part of a rigid electronic endoscope relating to the fifth embodiment of the present invention.

FIG. 7 is a sectioned view showing a small diameter part of an insertable part of a rigid electronic endoscope relating to the fifth embodiment of the present invention.

In this embodiment, the cross-sectioned shape of the outer pipe 42 is formed to be substantially elliptic.

In this embodiment, as shown in the drawing, the long diameter (of the outside diameter) of the above mentioned outer pipe 42 is formed to be substantially equal to the short diameter (of the inside diameter) of the hollow tube part 3 of the sheath 2 and the outer pipe 42 and hollow tube part 3 are so arranged that their long diameter directions may intersect at right angles with each other to form two hollow clearances above and below the above mentioned outer pipe 42. Therefore, one of these two hollow clearances is made a water feeding path and the other is made a water draining path so that a continuous irrigation may be possible.

Figure 8:
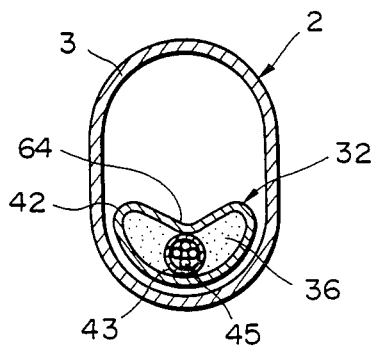
FIG. 8 is a sectioned view showing a small diameter part of an insertable part of a rigid electronic endoscope relating to the sixth embodiment of the present invention.

FIG. 8 is a sectioned view showing a small diameter part of an insertable of a rigid electronic endoscope relating to the sixth embodiment of the present invention.

In this embodiment, the cross-sectioned shape of the outer pipe 42 is formed to be substantially meniscus-like and the concave 64 on the upper surface is made a guide for the treating tool 55.

By the way, in the first to sixth embodiments, the treating tool raising device 50 may be provided.

The visual field direction is not limited to the forward oblique viewing but may be a straight viewing, side viewing and rearward oblique viewing.

Figure 9:
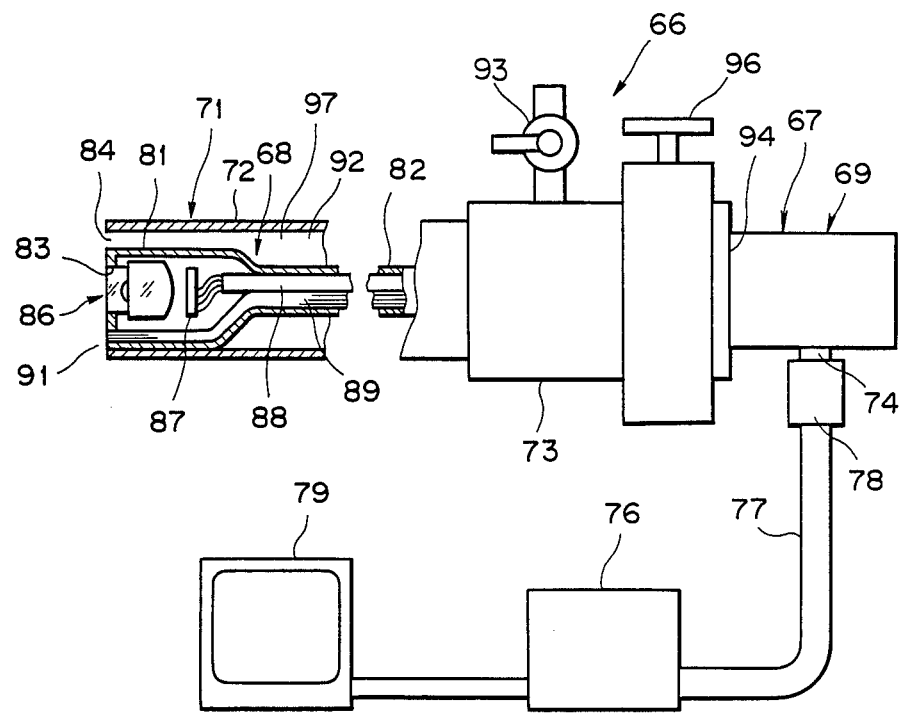
FIGS. 9 and 10 relate to the seventh embodiment of the present invention.
Figures 10, 11:
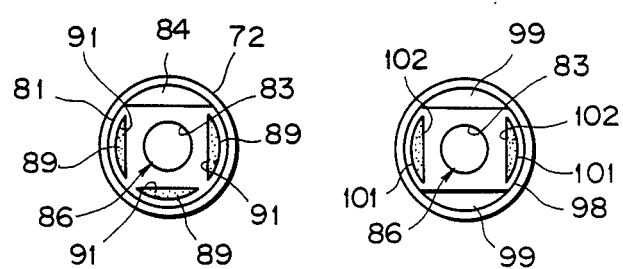
FIG. 11 relates to the eighth embodiment of the present invention and is an elevation of a tip part of a rigid electronic endoscope.

FIGS. 9 and 10 show the seventh embodiment of the present invention.

A rigid electronic endoscope apparatus 66 is formed as shown in FIG. 9.

A rigid electronic endoscope 67 has a rigid small diameter elongate insertable part 68 to the rear end part of which an operating part 69 is connected.

A light source and signal connecting connector receptacle 74 is provided on the side of the operating part 69 of the above mentioned rigid electroniic endoscope 67 and is connected with a light source and signal connecting connector 78 provided at the tip of a flexible universal cord 77 extended from a control apparatus 76 containing a light source apparatus and signal processing circuit.

Further, a color monitor 79 as a displaying means is to be connected to the above mentioned control apparatus 76.

The above mentioned insertable part 68 is made of a substantially tubular rigid member, for example, of a metal and comprises a large diameter tip part 81 and a small diameter insertable part body 82 connected to the rear of the tip part 81.

The above mentioned tip part 81 is made flat on a part of the outer peripheral surface to form a meniscus-like opening 84 between that part and the inner peripheral surface of a sheath inserting part 72.

An observing through hole 83 is provided in the lengthwise direction of the insertable part 68 in the center of the end surface of the above mentioned tip part 81 to fit an objective lens system 86.

A square solid state imaging device 87 having one side substantially parallel with the plane forming the above mentioned opening 84 is arranged in the image forming position of the above mentioned objective lens system 86. A signal line 88 is connected to the rear end surface of the solid state imaging device 87.

As shown in FIG. 10, meniscus-like guides 89 are arranged between the other three sides of the solid state imaging device 87 and the inner peripheral surface of the tip part 81 and are fitted into meniscus-like light guide through holes 91 provided on the end surface of the tip part 81.

The above mentioned light guides 89 are integrally combined into one in the rear of the solid state imaging device 87, are inserted together with the signal line 88 through the small diameter insertable part body 82 and are connected to the light source and signal connecting connector 74 provided on the operating part 69.

The sheath 81 internally inserting the above mentioned insertable part 68 has a rigid cylindrical sheath insertable part 72 having a connecting part 73 connected to the rear end part so that the above mentioned operating part 69 may be removably fitted by a removably fitting ring 96 provided in the rear end part of the connecting part 73.

A tube path 92 through which the insertable part 68 of the above mentioned rigid electronic endoscope 67 can be inserted is provided through the sheath insertable part 72 forming the above mentioned sheath 71 and the connecting part 73 so as to communicate with a removably fitting part 94 provided on the rear end surface of the connecting part 73.

An irrigating liquid feeding and draining cock 93 is provided on the side of the above mentioned connecting part 73 and is connected with such water feeding and draining path as a tube not illustrated.

Now, the irrigating liquid flowing in through the irrigating liquid feeding and draining cock 93 will pass through the irrigating liquid path 97 formed between the inner peripheral surface of the sheath insertable part 72 and the outer peripheral surface of the insertable part body 82 and will be able to be fed to the patient through the opening 84 formed between the tip part 81 and sheath insertable part 72. The irrigating liquid can be drained out of the body through the same course as is mentioned above.

As in this embodiment, when the insertable part body 82 through which the signal lines 88 and light guide 89 are inserted in the insertable part 68 of the rigid electronic endoscope 67 is made smaller in the diameter than the tip part 81, the irrigating path formed between the insertable part body 82 and the inner peripheral surface of the sheath insertable part 72 can be expanded without enlarging the outside diameter of the sheath insertable part 72.

By the way, in this embodiment, the imaging system is described as of a field sequential type but may be made a mosaic type imaging system by providing a color mosaic filter on the front surface of the solid state imaging device 87.

FIG. 11 shows the eighth embodiment of the present invention and is an elevation of a rigid electronic endoscope tip part.

In FIG. 11, planes are provided above and below on the outer peripheral surface of the tip part 98 of the insertable part 68 to form meniscus-like openings 99 between the planes and sheath insertable part 72.

An objective lens system 86 is fitted in an observing through hole in the center of the end surface of the tip part 98.

The planes forming the above mentioned meniscus-like openings 99 are substantially parallel with the upper and lower sides of a square solid state imaging device not illustrated provided in the rear of the above mentioned objective lens system 86. Light guides 101 are inserted between the other two sides and inner peripheral surface of the tip part 98 and are fitted into meniscus-like light guide through holes 102 provided on the end surface of the tip part 98.

As in this embodiment, by providing two openings 99, the amount of the fed and drained irrigating liquid can be made larger than in the seventh embodiment.

The other formations and operations are the same as in the seventh embodiment.

Figure 12:
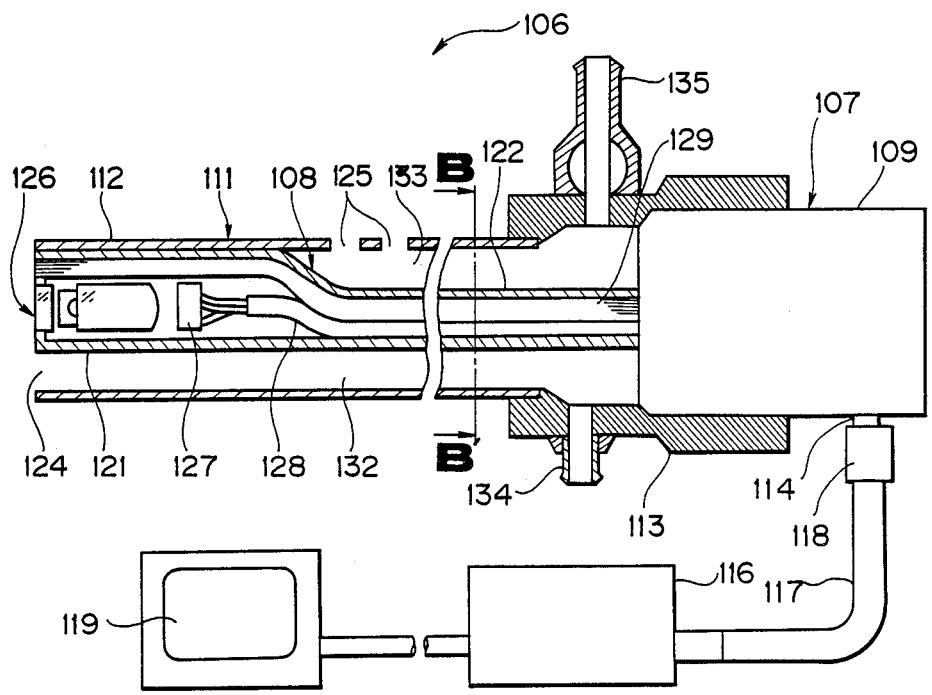
FIGS. 12 to 14 relate to the ninth embodiment of the present invention.
Figure 13:
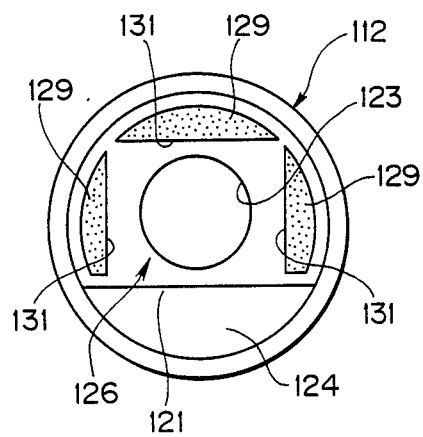
Figure 14:
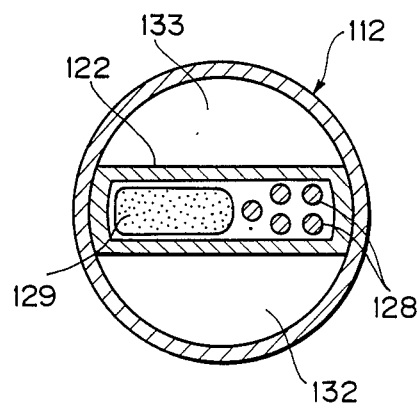

FIGS. 12 to 14 show the ninth embodiment of the present invention.

A rigid electronic endoscope apparatus 106 is formed as shown in FIG. 12.

A rigid electronic endoscope 107 has a rigid small diameter elongate insertable part 108 and an operating part 109 connected to the rear end of the insertable part 108.

A light source and signal connecting connector receptacle 114 is provided on the side of the operating part 109 of the above mentioned rigid electronic endoscope 107 and is connected with a light source and signal connecting connector 118 provided at the tip of a flexible universal cord 117 extended from a control apparatus 116 containing a light source apparatus and signal processing circuit.

Further, a color monitor 119 as a displaying means is to be connected to the above mentioned control apparatus 116.

The above mentioned insertable part 108 comprises a tip part 121 and an insertable part body 122. The tip part 121 is formed to be substantially semi-cylindrical with a plane lower surface. The insertable part body 122 of a lower surface flush with the tip part 121 and a lateral width of the same flat shape having a flat surface on the upper surface as of the tip part 121 is provided in the rear of the above mentioned tip part 121.

A liquid feeding part 124 opened to be like a meniscus is formed between the flat surface of the above mentioned tip part 121 and the inner peripheral surface of the sheath insertable part 112.

An objective lens system 126 is arranged in an observing through hole 123 provided in the lengthwise direction of the insertable part 108 in the center of the end surface of the above mentioned tip part 121.

A square solid state imaging device 127 having one side substantially parallel with the plane forming the above mentioned liquid feeding part is arranged in the image forming position of the above mentioned objective lens system 126. Signal lines 128 are connected to the rear end surface of the solid state imaging device 127.

As shown in FIG. 13, light guides 129 consisting of meniscus-like fiber bundles are inserted and provided between the other three sides than the lower surface of the solid state imaging device 127 and the inner peripheral surface of the tip part 121 and are inserted and arranged in meniscus-like light guide through holes 141 provided on the end surface of the above mentioned tip part 121.

Here, the above mentioned light guides 129 are integrally combined into one in the rear of the solid state imaging device 127, are inserted together with the signal lines 128 as shown in FIG. 14 through the insertable part body 122 made flat on the upper side and lower side and are connected to the light source and signal connecting connector 114 fitted to the operating part 109.

The sheath 111 internally inserting the above mentioned insertable part 108 has a rigid cylindrical sheath insertable part 112 connected at the rear end with a removably fitting part 113 which can removably fit the above mentioned operating part 109.

This sheath insertable part 112 has liquid sucking parts 125 opened in the rear upper part of the tip part 121 of the insertable part 108 of the rigid endoscope.

A liquid feeding mouthpiece 134 to be fitted with a tube or the like not illustrated for feeding an irrigating liquid is provided to project on the lower side of the above mentioned removably fitting part 113 and a liquid sucking mouthpiece 135 to be fitted with a tube or the like not illustrated for draining the liquid is provided to project on the upper side of the above mentioned removably fitting part 113.

The endoscope insertable part 108 comprising the semicylindrical tip part 121 and flat insertable part body 122 is inserted through the sheath insertable part 112. These tip part 121 and insertable part body 122 section the sheath insertable part 112 interior above and below in the illustrated example as a partition part to form a liquid sucking tube path 133 on the upper side and a liquid feeding tube path 132 on the lower side.

The above mentioned liquid sucking tube path 133 communicates on the base side with the liquid sucking joint 135 provided on the removably fitting part 113 and on the tip side with the liquid sucking parts 125 formed on the upper surface of the sheath insertable part 112 in the rear of the tip part 121.

Further, the liquid feeding tube path 132 communicates on the base side with the liquid feeding joint 134 provided on the removably fitting part 113 and at the tip with the liquid feeding part 124 on the tip surface of the sheath insertable part 112.

Therefore, the irrigating liquid flowing in through the liquid feeding joint 134 will pass through the above mentioned liquid feeding tube path 132 and will be fed to the affected part through the liquid feeding part 124. In the case of draining this irrigating liquid, the irrigating liquid will be sucked through the liquid sucking parts 125, will pass through the liquid sucking tube path 133 and will be drained out of the body through the liquid sucking joint 135.

That is to say, according to the ninth embodiment of the present invention, when the insertable part body 122 through which the signal lines 128 and light guide 129 are inserted in the insertable part 108 of the rigid electronic endoscope 107 is made flatter and thinner than the tip part 121 and is used as a partition part of the liquid feeding tube path 132 and liquid sucking tube path 133, a further sufficient continuous irrigation will be able to be made without enlarging the outside diameter of the sheath insertable part.

Figure 15:
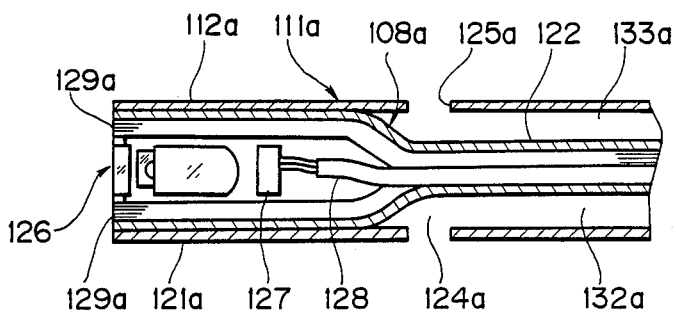
FIGS. 15 and 16 relate to the tenth embodiment of the present invention.
Figure 16:
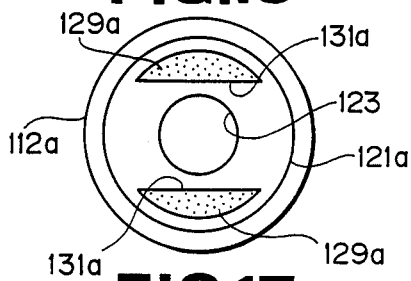

FIGS. 15 and 16 relate to the tenth embodiment of the present invention. FIG. 15 is a sectioned view showing the formation of the tip side of a rigid electronic endoscope apparatus. FIG. 16 is a magnified elevation of the tip surface of the rigid electronic endoscope apparatus.

In FIG. 15, an insertable part 108a comprises a cylindrical tip part 121a and a flat insertable part body 122 provided in the rear of this tip part 121a.

An objective lens system 126 is arranged in an observing through hole 123 provided in the lengthwise direction of the insertable part 108a in the center of the end surface of the above mentioned tip part 121a.

A square solid state imaging device 127 is arranged in the image forming position through the image forming optical system of the above mentioned objective lens system 126. Signal lines 128 are connected to the rear end of the above mentioned solid state imaging device 127. As shown in FIG. 16, light guides 129a consisting of meniscus-like fiber bundles are inserted and provided between the upper and lower sides of this solid state imaging device 127 and the inner peripheral surface of the tip part 121a and are fitted into meniscus-like light guide through holes 131a provided on the end surface of the above mentioned tip part 121a.

Here, the above mentioned light guides 129a are integrally combined into one in the rear of the solid state imaging device 127, are inserted together with the signal lines 128 through the flattened insertable part body 122 as in FIG. 14 and are connected to a light source and signal connecting connector not illustrated fitted to an operating part not illustrated. A sheath 111a internally fitting the above mentioned insertable part 108a has a liquid feeding part 124a and a liquid sucking part 125a opened respectively, for example, on the lower side and upper side near the above mentioned tip part 121a in the sheath insertable part 112a in the rear of the tip part 121a of this insertable part 108a.

Further, when the insertable part body 122 extended rearward of the above mentioned insertable part 108a is inserted into the sheath insertable part 112a as in FIG. 14, the flat side will contact the inner peripheral surface and this insertable part body 122 will become a partition part to form a meniscus-like liquid feeding tube path 132a on the liquid feeding part 124a side an a meniscus-like liquid sucking tube path 133a on the liquid sucking part 125a side.

Therefore, the irrigating liquid will pass through the above mentioned liquid feeding tube path 132a and will be able to be fed to the affected part through the liquid feeding part 142a. In the case of draining this irrigating liquid, it will be drained through the liquid sucking tube path from the liquid sucking part.

The other formations and effects in the tenth embodiment are the same as in the ninth embodiment.

Figure 17:
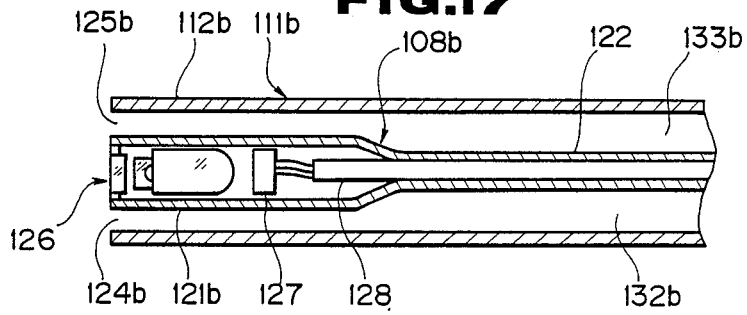
FIGS. 17 and 18 relate to the eleventh embodiment of the present invention.
Figure 18:
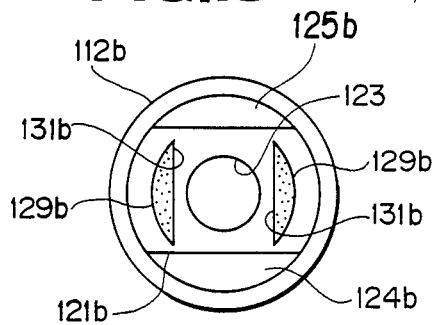

FIGS. 17 and 18 relate to the eleventh embodiment of the present invention. FIG. 17 is a sectioned view showing the formation of the tip side of a rigid electronic endoscope apparatus. FIG. 18 is a magnified elevation of the tip surface of the rigid electronic endoscope apparatus.

In FIG. 17, an insertable part 108b comprises a tip part 121b made flat above and below and a flatter and thinner insertable part body 122 than this tip part 121b.

The objective lens system 126, solid state imaging device 127 and signal lines 128 provided within the above mentioned tip part 121b are of the same formation as in the ninth embodiment.

As shown in FIG. 18, light guides 129b consisting of meniscus-like fiber bundles are inserted and provided on the sides of the above mentioned tip part 121b and are fitted in light guide through holes 131b.

Further, as in FIG. 14, when the above mentioned insertable part 108b and insertable part body 122 are inserted into the sheath insertable part 112b, the flat side will contact the inner peripheral surface of the sheath insertable part 112b and the insertable part 108b and insertable part body 122 will become a partition part to form a liquid feeding tube path 132b, for example, below and a liquid sucking tube path 133b above. A liquid feeding part 124b opens on the front end surface of the above mentioned liquid feeding tube path 132b and a liquid sucking part 125b opens on the front end surface of the above mentioned liquid sucking tube path 133b.

Therefore, the irrigating liquid will pass through the above mentioned liquid feeding tube path 132b and will be able to be injected onto the affected part through the liquid feeding part 124b. In the case of draining this irrigating liquid, it will be drained through the liquid sucking tube path 133b from the liquid sucking part 125b.

The other formations and effects in the eleventh embodiment are the same as in the ninth embodiment.

By the way, in this embodiment, the imaging system is described as of a field sequential type but may be made a mosaic type imaging system by providing a color mosaic filter on the front surface of the endoscope solid state imaging device 127.

FIGS. 19 to 22 show the twelfth embodiment of the present invention.

This embodiment is to apply the present invention to an electronic resectoscope.

In FIG. 19, a rigid electronic endoscope apparatus 136 is formed of an electronic resectoscope 137, an elongate hollow sheath 138, a light guide and signal cable 139 removably connected to the rear end of the above mentioned electronic resectoscope 137, a control apparatus 141 connected with the above mentioned electronic resectoscope 137 through this light guide and signal cable 139 and containing a light source part and video signal processing part and a monitor 142 in which a video signal from this control apparatus 141 can be input to display an observed image.

The above mentioned electronic resectoscope 137 is formed of a handle 144 to be connected to a sheath body 143 having an elongate hollow tube part 147 to be inserted into a urethra connected forward an an electrode device 146 inserted through the hollow tube part 147 from the above mentioned handle 144 as combined.

The above mentioned hollow tube part 147 has an insulating beak 147a connected to the tip part. By the way, the hollow tube part 147 may be formed of an insulating material integrally with the insulating beak 147a.

The above mentioned sheath body 143 has a water feeding part 149 fitted with a cock 148 feeding an irrigating liquid into a bladder through the hollow tube part 147 and a drain part 153 fitted with a cock 152 draining this fed irrigating liquid through sucking holes 151 and the hollow tube part 147, has a fitting part 156 fitting a connecting part 154 of the handle 144 and is provided with an engaging button 157 engaging, for example, a clicking mechanism for fixing this connecting part 154 within the fitting part 156.

An insertable part 158 inserted through the hollow tube part 147 and leading to the inside of the tip of this hollow tube part 147 is extended forward of the connecting part 154 provided on the above mentioned handle 144. The connecting part 154 of this handle 144 is provided with a hollow guide shaft 159 to project rearward in the axial direction and has a slider stopper 161 fixed at the rear end of this guide shaft 159. On the other hand, a slider 162 sliding in the axial direction along a guide shaft 159 is arranged between the above mentioned connecting part 154 and slider stopper 161 and is energized to contact, for example, the slider stopper 161 and return by a spring 163 provided between the slider 162 and connecting part 154. By the way, the above mentioned spring 163 is a plate spring in the illustrated example but may be a coil spring or may not be provided. The connecting part 154 of the above mentioned handle 144 is provided with finger hangers 164 and 166 to project respectively above and below and the slider 162 also has a thumb hanger 167 in the rear below.

The above mentioned slider 162 has an electrode device fixing part 168 in which an electrode device 146 is inserted from the front and is removably fixed and a connector 169 for passing a high frequency current from a high frequency cautery current source to this connected electrode device 146 is provided to project. The electrode device 146 fixed to this slider 162 and provided to project forward projects forward through an inserting hole not illustrated formed in the connecting part 154 of the handle 144.

The above mentioned electrode device 146 consists, for example, of a loop-like resecting tip electrode 171 at the tip and a shaft part 172. When a high frequency current is passed through this resecting tip electrode 171, such treatment as resecting or incising an affected part (such as a prostate) or stopping bleeding will be made. The shape and formation of the above mentioned resecting tip electrode 171 may be any others than are illustrated.

Figure 21:
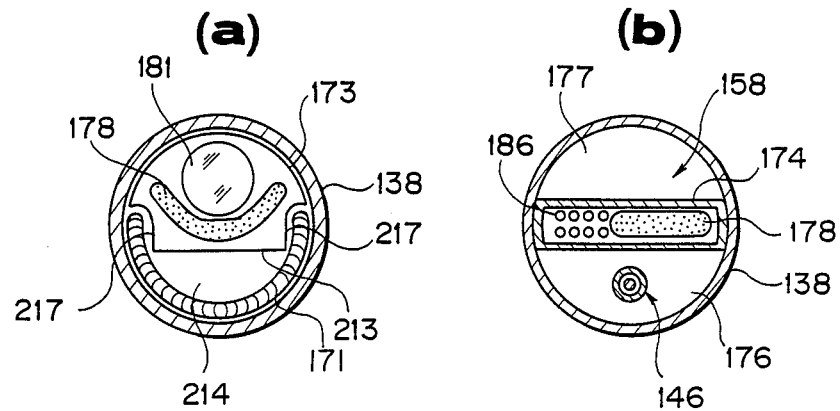

In FIG. 21, the insertable part 158 of the above mentioned handle 144 is formed of a thick tip part 173 (FIG.

21a) and a flat partition part 174 (FIG. 21b) provided in the rear of this tip part 173.

The above mentioned partition part 174 divides the hollow tube part 147 interior in the axial direction into two parts, the lower part side being made an inserting path 176 through which such treating tool as the above mentioned electrode device can be inserted and an irrigating liquid can be fed and the upper part side being made a drain path draining the irrigating liquid. The tip part 173 is partly incised on the outer periphery on a column to form a plane part 213. A water feeding space 214 formed by this plane part 213 and the inner surface of the hollow tube part 147 communicates with the above mentioned inserting path 176. By the way, the front part of the above mentioned drain path 177 is to be closed by the other tip part 173 than the plane part 213. This drain path 177 communicates with sucking holes 151 provided near the rear of the tip part 173 on the side surface of the hollow tube part 147 so that the irrigating liquid fed, for example, into a body cavity may be drained out of the body cavity. Further, as in FIG. 21(a), the tip part 173 is provided on the right and left sides with groove parts 217 which can contain a resecting tip electrode 171 formed in the tip part of the electrode device 146 inserted through the inserting path 176 so that the resecting tip electrode 171 may be slidably held by these groove parts 217.

In FIG. 20, a lens frame 179 holding an observing optical system is arranged on the tip part side within the above mentioned tip part 173, a cover glass 181 is arranged at the tip of this lens frame 179 and an objective lens system 180 as an image forming optical system is posted, for example, with a bonding agent in the ear of this cover glass 181. A solid state imaging device (abbreviated as CCD hereinafter) 183 positioned by a spacer 182 is provided in the image forming position in the rear of this objective lens system 180 and further an amplifying part 184 amplifying electric signals obtained by this CCD 183 an signal lines 186 which can transmit driving pulses of this CCD 183 and electric signals obtained by the CCD 183 are connected to the back surface of the CCD 183. The exit end surface of a light guide 178 which can illuminate the observed position is provided on the tip surface of the tip part 173 so that the illuminating light may be emitted.

The light guide 178 and signal lines 186 within the above mentioned insertable part 158 are further extended through the hollow guide shaft 159 in the rear of the handle 144 and are connected to a light guide and signal connector 187 provided at the rear end of the slider stopper 161 and having an electric system socket and light guide entrance end. Further, the above mentioned light guide and signal cable 139 having a flexibility is connectable to this light guide and signal connector 187 through a connector receptacle 188. The above mentioned light guide 178 and signal lines 186 are extended through this light guide and signal cable 139 which is provided at the other end with a connector 189 having an electric system socket 189a and illuminating system socket 189b.

The control apparatus 141 containing the light source part 191 and video signal processing circuit 192 has an electric system connector receptacle 193 and illuminating system connector receptacle 194 to be connected with the sockets 189a and 189b of the above mentioned connector 189. A monitor 142 as a displaying means is to be connected with this control apparatus 141.

Figure 22:
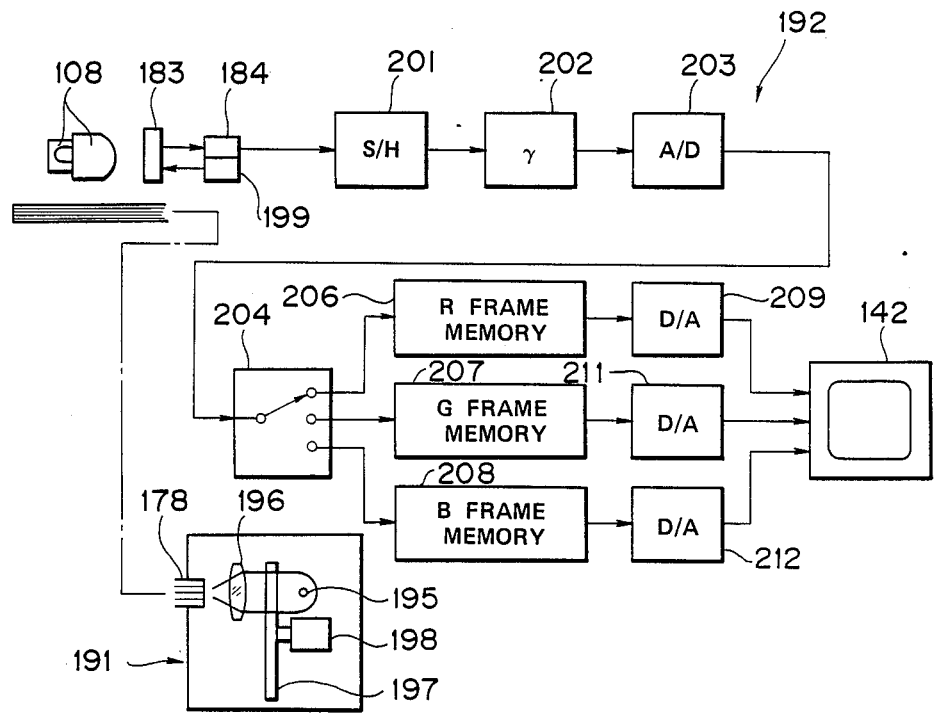

FIG. 22 is a block diagram of a video signal processing circuit of a field sequential system.

In FIG. 22, a light source part 191 provided within the above mentioned control apparatus 141 is provided with a light source lamp 195 and a rotary color filter 197 having color transmitting filters for three primary colors of red, green and blue. This rotary color filter 197 is rotated and driven, for example, by a stepping motor 198. The illuminating light of the above mentioned light source lamp 195 provides light of respective wavelengths of red, green and blue in turn through the above mentioned rotary color filter 197. This light is condensed by a condenser lens 196 and is emitted from the tip of the insertable part 158 of the handle 144 through the light guide 178 within the above mentioned light guide and signal cable 139 to illuminate the observed position in the color frame sequence.

The reflected lights corresponding to the respective color lights of red, green and blue from the above mentioned observed position will pass through an objective lens system 180 and will be received on the image area of an imaging chip not illustrated embedded within a CCD 183. The output signal from the image area of this imaging chip not illustrated will be output in turn, for example, in the lateral direction from the CCD 183 by a clock signal applied from a driving circuit 199. The electric signal containing this picture information will be amplified by an amplifying part 184 and a video signal will be extracted in a sample holding circuit 201, will be further γ-corrected by a γ-correcting circuit 202 and will be converted to a digital signal by an A/D converter 203. This electric signal will be repeated as synchronized with a color frame sequential illumination by a multiplexer 204 and will be memorized in turn in an R frame memory 206, G frame memory 207 and B frame memory 208 corresponding to the respective colors of red, green and blue. The above mentioned respective frame memories 206, 207 and 208 will be read out simultaneously in the lateral direction at a speed matching the monitor 142 and will be converted to analogue signals respectively by D/A converters 209, 211 and 212 so as to be R, G and B color signals. When these R, G and B signals are input into the monitor 142, the observed position will be color-displayed.

Thus, in the rigid electronic endoscope apparatus 136 of this embodiment, the insertable part 158 through which the light guide 178 and signal lines 186 are inserted is provided with a flat partition part 174 to divide the sheath 138 interior in the axial direction into two parts forming an inserting path 176 and drain path 177 so that the hollow clearance between the sheath 138 and insertable part 158 may be larger than before and therefore an electrode device 146 thicker than before may be used without making the hollow tube part 147 of the sheath 138 thicker. Further, as the irrigating liquid is fed to the inserting path 176 and is drained from the drain path 177, the irrigating liquid can be continuously fed and the affected part can be well observed.

FIG. 23 is of a modification of the above mentioned twelfth embodiment and is an explanatory view explaining a video signal processing circuit of an electronic scope adopting a simultaneous system.

In this modification, a color mosaic type optical filter 221 is arranged on the front surface of a CCD 183 arranged in the image forming position of an objective lens system 180.

On the other hand, a mosaic type process circuit 222 and light source apparatus 223 are provided within a control apparatus 141. The light source apparatus 223 is formed of a light source lamp 195 and condenser lens 196. The white light emitted from the above mentioned light source lamp 195 will be condensed by the above mentioned condenser lens 196, will enter a light guide 178 consisting of a fiber bundle within the above mentioned light guide and signal cable 139 and will be emitted from the tip of the insertable part 158 of the handle 144 to illuminate the observed position. The white light reflected from this observed position will pass through the objective lens system 180, will be divided into respective colors of red, green and blue by a color mosaic type optical filter 221 arranged in front of a CCD 183 and will be received by an image area of an imaging chip. The electric signal containing the picture information from this imaging chip will be synchronized with a clock signal applied from a driving circuit 199, will be output in turn, for example, in the lateral direction, will be amplified by an amplifying part 184 and will be input into a luminance signal processing circuit 224 and color signal reproducing circuit 226. A luminance signal Y will be provided from the luminance signal processing circuit 224. Color difference signals R-Y and B-Y will be produced in each horizontal line in time series from the color signal reproducing circuit 226 and will be compensated in the white balance by a white balance circuit 227. The output of this white balance circuit 227 will be branched, one branch will be input into an analogue switch 230 and the other will be delayed by one horizontal line by a 1H delay line 228 and will be input into an analogue switch 229. The analogue switches 229 and 230 will be switched by switching signals of a timing generator not illustrated to produce color difference signals R-Y and B-Y. The above mentioned luminance signal Y and color difference signals R-Y and B-Y will be multiplexed by an NTSC encoder 231 and will be input into a monitor 142 to color-display the observed position.

The other formations, operations and effects are the same as in the twelfth embodiment.

FIGS. 24 and 25 show the thirteenth embodiment of the present invention.

This embodiment is to apply the present invention to a rigid electronic endoscope apparatus.

A rigid electronic endoscope 234 of this embodiment is to be used in combination with a sheath 236. As shown in FIG. 25, the above mentioned sheath 236 has an elongate hollow tube part 238, for example, substantially circular in the cross-section. An observing and treating tool opening 237 is formed from the tip to the upstream side in the tip part of this hollow tube part 238. A connecting part 239 which can removably connect the above mentioned rigid electronic endoscope 234 is provided at the rear end of the above mentioned sheath 236, is provided with a water feeding part 241 which can feed an irrigating liquid into the sheath 236 and can be opened and closed by a cock 242 and is further provided with a drain part 243 which can drain out of the body cavity the irrigating liquid fed through the above mentioned water feeding part and can be opened and closed by a cock 244.

On the other hand, the above mentioned rigid electronic endoscope 234 is provided with an operating part 247 provided at the rear end of the rigid elongate insertable part 158 inserted through then hollow tube part 238 of the above mentioned sheath 236. The above mentioned operating part 247 is provided at the front end with a tapered part 248 thinner on the tip side to be fitted into the connecting part 239 of the above mentioned sheath 236 and a connecting part 249 to be connected with the above mentioned connecting part 239 adjacently in the rear of this tapered part 248 and is provided on the rear end side with a wire operating knob 251 and a light guide mouthpiece 252 which is also a signal connector. A light guide cable 253 through which a signal cable is inserted is to be connected to the above mentioned light guide mouthpiece 252 and is to be connected to a control apparatus not illustrated containing a light source apparatus and signal processing circuit.

The above mentioned operating part 247 is provided with a treating tool inserting part 256 having an inserting part 255 through which a flexible treating tool 260 can be inserted as branched obliquely rearward with respect to the axial direction of the insertable part 158. By the way, this inserting part 255 can be opened and closed by a cock 255a.

The above mentioned insertable part 158 is provided with a thick tip part 257 and a flat partition part 174 provided in the rear of this tip part 257. By the way, the above mentioned partition part 174 is positioned in the center within the hollow tube path 238 of the sheath 236 so as to divide the sheath 236 interior in the axial direction into two parts. The tip part 257 is formed to close the tip part side of one of the two spaces divided by the partition part 174.

The above mentioned tip part 257 is provided with a rigid tip part body 259. A sloped opening 261 opening on the opening 237 side of the above mentioned sheath 236 is formed at the tip of this tip part body 259. A cover glass 263 and the tip part of the light guide (of fibers) 178 are inserted and fitted in this opening 261. An objective lens system 264 in which the observing visual field direction as opposed to the above mentioned cover glass 263 is set in an oblique forward direction so as to have a predetermined angle with the axial direction of the insertable part 158 in response to the opening 237 of the above mentioned sheath 236 is contained within the above mentioned tip part body 259. A CCD 183, is arranged in the image forming position of this objective lens system 264.

As shown in FIG. 25, the light guide 178 and the signal lines 186 connected to the solid state imaging device (abbreviated as CCD 183 hereinafter) are inserted through the above mentioned partition part 174 which is to divide the sheath 236 interior into two parts. One of the two divided spaces formes an inserting path 176 through which a treating tool or the like can be inserted and makes the opening 237 communicate with the above mentioned water feeding part 241 and treating tool inserting part 255. The other of the two divided spaces forms a drain path 177 capable of draining the irrigating liquid and makes the drain part 243 communicate with the sucking holes 151 which can suck the irrigating liquid and are provided on the outer periphery of the sheath 236 in the rear of the tip.

Also, in this embodiment, a treating tool raising device (also called a heaver) 266 is provided on the side corresponding to the opening 237 of the above mentioned sheath 236 in the above mentioned tip part 257. This treating tool raising device 266 is provided with a raising stand 268 rotatable on the tip side with a rotary shaft 267 as a center and, for example, two operating wires 269 connected to this raising stand 268 and operating to rotate it. The above mentioned operating wires 269 are connected to a wire operating knob 251 as inserted through a wire pipe 269a parallelly provided in the lower part of the insertable part 158. When this wire operating knob 251 is operated to rotate, the above mentioned raising stand 268 will be rotated, a flexible treating tool 260 will be raised on the tip side and, in the direction position of the tip part 257, the above mentioned flexible treating tool 260 will be able to be projected sidewise in the tip part out of the opening 237 of the above mentioned sheath 236.

By the formation as in this embodiment, a treatment can be made with the flexible treating tool 260 while continuously running the irrigating liquid.

The other formations, operations and effects are the same as in the twelfth embodiment.

FIGS. 26 and 27 show the fourteenth embodiment of the present invention.

A rigid electronic endoscope 271 of this embodiment is to be used as combined with a sheath 272. The above mentioned sheath 272 has an elongate hollow tube part 238, for example, substantially circular in the cross-section. This sheath 272 is provided in the rear end part with a connecting part 276 which can removably connect the above mentioned rigid electronic endoscope 271. This connecting part 276 is provided with a water feeding part 277 which can feed an irrigating liquid into the sheath 272 so that this water feeding part 277 may be opened and closed by a cock 278. The connecting part 276 is further provided with a drain part 279 which can drain the irrigating liquid fed into the body cavity and coming from this water feeding part 277 and can be opened and closed by a cock 281.

The insertable part 158 of the rigid electronic endoscope 271 inserted through the above mentioned sheath 272 is provided with a tip part 173 and partition part 174 the same as in the twelfth embodiment. As in FIG. 25, this partition part 174 divides the sheath 272 interior into two parts to form an inserting path 176 and drain path 177. An operating part 282 is provided in the rear end part of this insertable part 158. A connecting part 283 provided in the front end part of this operating part 282 is fitted in a connecting part 276 of the above mentioned sheath 272 to be removably connected. a light guide cable 253 through which signal cables are inserted is connected to the side of this operating part 282. A treating tool inserting part 286 into which a rigid treating tool 284 can be inserted parallel with the axial direction of the insertable part 158 and which is provided with an inserting part 255 communicating with the above mentioned inserting path 176 is provided at the rear end of the operating part 282. By the way, the treating tool inserting part 286 is provided with a cock 255a which can open and close the inserting part 255.

In this embodiment, as the inserting path 176 and treating tool inserting part 255 communicate with each other and further the treating tool can be inserted in the axial direction of the insertable part 158, the treatment can be made with the rigid treating tool 284 while continuously running the irrigating liquid.

In the above mentioned respective embodiments, as the cross-sectional shape of the insertable part on the base side is made smaller than the cross-sectioned shape of the tip part in which the solid state imaging device as an imaging means is provided, a path large enough to insert a treating tool or irrigating liquid can be secured between the sheath and insertable part and a treating tool of a large diameter can be used without using a sheath of a large diameter.

Further, as the sheath interior is divided into two parts by forming a partition part on the base side of the insertable part, a large amount of an irrigating liquid can be continuously fed and drained.

What is claimed is:

1. A rigid electronic endoscope comprising:
    a rigid hollow insertable part of substantially constant hollow cross sectional area having a tip end and a base end;
    an operating part provided at said base end of said insertable part;
    a tip part provided at the tip end of said insertable part, said tip part being of cross sectional area substantially equal to said insertable part hollow cross sectional area and including a solid state imaging device provided as an imaging means for said endoscope; and
    a supporting part for said tip part forming an inner pipe extending axially through said insertable part between said tip end and said base end, said supporting part accommodating therewithin signal lines for said imaging device and having a cross sectional area substantially less than said hollow cross sectional area of said insertable part, such that major hollow cross sectional area space remains for passage therethrough of treating means.

2. A rigid electronic endoscope according to claim 1 wherein a treating tool raising device is provided on the tip end of said supporting part adjacent said tip part.

3. A rigid electronic endoscope according to claim 1 wherein said insertable part is inserted through an eccentric position within a guide tube.

4. A rigid electronic endoscope according to claim 1 wherein said supporting part has a flat part and has a cross-sectioned shape formed to be substantially semicircular.

5. A rigid electronic endoscope according to claim 4 wherein said supporting part is formed to be substantially semicircular by said flat part and has a cross-sectioned shape provided with convexes on the edges of said flat part.

6. A rigid electronic endoscope according to claim 1 wherein said supporting part has a cross-sectioned shape formed to have two concaves in the axial direction.

7. A rigid electronic endoscope according to claim 1 wherein said supporting part has a cross-sectioned shape formed to be substantially elliptic.

8. A rigid electronic endoscope according to claim 1 wherein said supporting part has a cross-sectioned shape formed to be substantially meniscus-like.

9. A rigid electronic endoscope comprising:
    a rigid hollow insertable part of substantially constant hollow cross sectional area having a tip end and a base end;
    an operating part provided at said base end of said insertable part;
    a rigid elongate guide tube through which said insertable part is inserted such that a space is provided between said insertable part and said guide tube;
    a tip part provided at the tip end of said insertable part, said tip part being of cross sectional area substantially equal to said insertable part hollow cross sectional area and including a solid state imaging device provided as an imaging means for said endoscope; and
    a supporting part for said tip part forming an inner pipe extending axially through said insertable part between said tip end and said base end, said supporting part accommodating therewithin signal lines for said imaging device and having a cross sectional area substantially less than said hollow cross sectional area of said insertable part, such that major cross sectional area space remains for passage therethrough of treating means.

10. A rigid electronic endoscope according to claim 9 wherein said space is an irrigating liquid path.

11. A rigid electronic endoscope according to claim 9 wherein said space is a treating tool path.

12. A rigid electronic endoscope according to claim 9 wherein said space is a fluid path.

13. A rigid electronic endoscope according to claim 9 wherein said guide tube is a sheath 14. A rigid electronic endoscope according to claim 9 wherein said insertable part is inserted through an eccentric position within said guide tube.

15. A rigid electronic endoscope according to claim 9 wherein a treating tool raising device is provided on the tip end of said supporting part adjacent said tip part.

16. A rigid electronic endoscope according to claim 9 wherein said supporting part has a flat part and has a cross-sectioned shape formed to be substantially semicircular.

17. A rigid electronic endoscope according to claim 16 wherein said supporting part is formed to be substantially semicircular by said flat part and has a cross-sectioned shape provided with convexes on the edges of said flat part.

18. A rigid electronic endoscope according to claim 9 wherein said supporting part has a cross-sectioned shape formed to have two concaves in the axial direction.

19. A rigid electronic endoscope according to claim 9 wherein said supporting part has a cross-sectioned shape formed to be substantially elliptic.

20. A rigid electronic endoscope according to claim 9 wherein said supporting part has a cross-sectioned shape formed to be substantially meniscus-like.

21. A rigid electronic endoscope comprising:

a rigid insertable part having a tip end and a base end;
an operating part provided at said base end of said insertable part;
a guide tube having a hollow part of substantially constant cross sectional area through which said insertable part is inserted;
a tip part provided at the tip end of said insertable part, said tip part being of cross sectional area less than said guide tube cross sectional area and including a solid state imaging device provided as an imaging means for said endoscope; and
a supporting part for said tip part forming a inner pipe of substantially less cross sectional area then said tip part extending axially through said guide tube, wherein said supporting part is formed to be flat and thin and so arranged to divide said hollow part into two parallel hollow parts.

22. A rigid electronic endoscope according to claim 21 wherein said guide tube forms an opening communicating between said base end and said tip end.

23. A rigid electronic endoscope according to claim 22 wherein said guide tube has an opening communicating with said hollow part on the outer peripheral surface.

24. A rigid electronic endoscope according to claim 22 wherein said hollow part is an irrigating liquid path.

25. A rigid electronic endoscope according to claim 22 wherein either one part of said hollow parts forms an irrigating liquid path which can feed and drain an irrigating liquid.

26. A rigid electronic endoscope according to claim 22 wherein said hollow part forms a treating tool path.

27. A rigid electronic endoscope according to claim 22 wherein said tip part closes either one of said hollow parts.

28. A rigid electronic endoscope according to claim 22 wherein one of said hollow parts forms an irrigating liquid path which can feed an irrigating liquid and the other forms an irrigating liquid path which can drain the irrigating liquid.

* * * * *